(12) United States Patent
Kessell et al.

(10) Patent No.: US 7,874,308 B2
(45) Date of Patent: *Jan. 25, 2011

(54) ROTATING VALVE ASSEMBLY

(75) Inventors: Michael Ross Kessell, Auckland (NZ);
Paul Neville Adams, Auckland (NZ);
Steven Lyle Weir, Auckland (NZ);
Henry Bolanos, Norwalk, CT (US)

(73) Assignee: Axial Technologies, Limited, Northcote, Auckland (NZ)

( * ) Notice: Subject to any disclaimer, the term of this patent is extended or adjusted under 35 U.S.C. 154(b) by 546 days.

This patent is subject to a terminal disclaimer.

(21) Appl. No.: 11/640,009

(22) Filed: Dec. 15, 2006

(65) Prior Publication Data

US 2008/0157018 A1    Jul. 3, 2008

Related U.S. Application Data

(63) Continuation of application No. 10/856,011, filed on May 28, 2004, now Pat. No. 7,165,568.

(60) Provisional application No. 60/516,569, filed on Oct. 31, 2003.

(30) Foreign Application Priority Data

May 29, 2003  (NZ) ...................................... 526158

(51) Int. Cl.
*F16K 17/14* (2006.01)
*F16K 35/00* (2006.01)
*A61M 5/178* (2006.01)

(52) U.S. Cl. .............. 137/68.3; 137/68.19; 251/317.01; 251/352; 222/153.06; 604/167.05

(58) Field of Classification Search .............. 137/68.19, 137/68.3, 551, 625.32; 251/315.01, 314.14, 251/317.01, 352; 222/153.06, 153.07, 507; 604/167.05, 248

See application file for complete search history.

(56) References Cited

U.S. PATENT DOCUMENTS

| 133,215 A | 11/1872 | Endicott |
|---|---|---|
| 2,120,510 A | 6/1938 | Rhoads |
| 2,495,015 A | 1/1950 | McGrath |

(Continued)

FOREIGN PATENT DOCUMENTS

| EP | 0820813 A2 | 1/1998 |
|---|---|---|
| EP | 1433712 A1 | 6/2004 |
| EP | 1439339 | 7/2004 |
| WO | WO 98/03410 | 1/1998 |
| WO | WO 02/029303 | 4/2002 |
| WO | WO 2004/106782 A2 | 9/2004 |

*Primary Examiner*—John Rivell
(74) *Attorney, Agent, or Firm*—Jacobson Holman PLLC

(57) ABSTRACT

A valve/seal assembly that is adapted for use in a variety of applications, such as for example, medical, consumer beverage, pharmaceutical containers, automobile, household appliance and marine. The valve includes, a valve housing having an upper body portion and a lower body portion and a generally spherical valve member. The upper and lower body portions of the housing define an internal chamber for accommodating the valve member and a central axis for the valve. The generally spherical valve member is seated within the internal chamber of the valve housing and has an axial bore extending therethrough. The valve member is mounted for movement between an open position; wherein the axial bore of the valve member is axially aligned with the inlet and outlet ports of the valve housing, and a closed position; wherein the axial bore of the valve member is out of alignment with the inlet and outlet ports of the valve housing. The valve assembly further includes a camming mechanism that is operatively associated with the valve housing and the valve member for moving the valve member between the open position and the closed position.

34 Claims, 12 Drawing Sheets

U.S. PATENT DOCUMENTS

| | | |
|---|---|---|
| 3,397,712 A | 8/1968 | Boroson |
| 3,690,521 A | 9/1972 | Middleton |
| 3,703,249 A | 11/1972 | Middleton |
| 3,703,250 A | 11/1972 | Middleton |
| 4,141,476 A | 2/1979 | Rech |
| 4,212,321 A | 7/1980 | Hulsey |
| 4,262,691 A | 4/1981 | Kacal |
| 4,540,411 A | 9/1985 | Bodicky |
| 4,634,098 A | 1/1987 | Varden |
| 4,867,414 A | 9/1989 | Hubacek |
| 4,971,227 A | 11/1990 | Knickerbocker et al. |
| 5,242,151 A | 9/1993 | Boehm et al. |
| 5,265,845 A | 11/1993 | Gilliam |
| 5,308,039 A | 5/1994 | King |
| 5,478,318 A | 12/1995 | Yoon |
| 5,743,437 A | 4/1998 | Moore et al. |
| 6,595,946 B1 | 7/2003 | Pasqualucci |
| 6,615,760 B1 | 9/2003 | Wise et al. |
| 6,695,285 B1 | 2/2004 | Hotton et al. |
| 6,758,359 B2 | 7/2004 | Yurkewicz et al. |
| 7,165,568 B2 * | 1/2007 | Kessell et al. ............... 137/68.3 |
| 2004/0256004 A1 | 12/2004 | Kessell et al. |

* cited by examiner

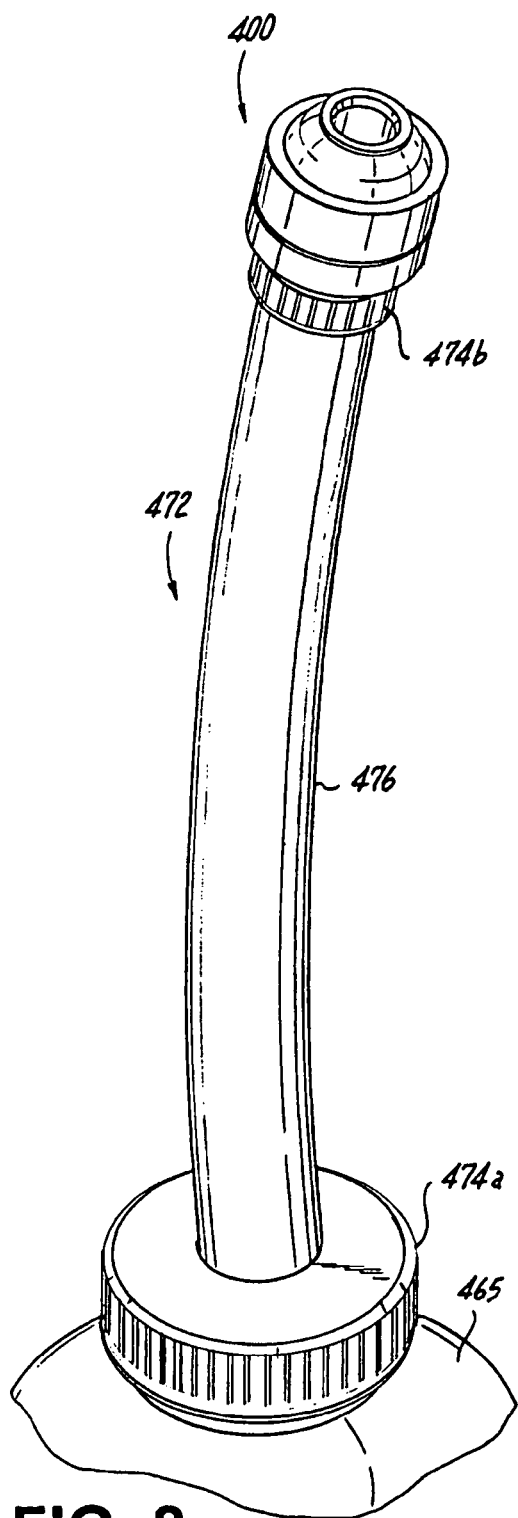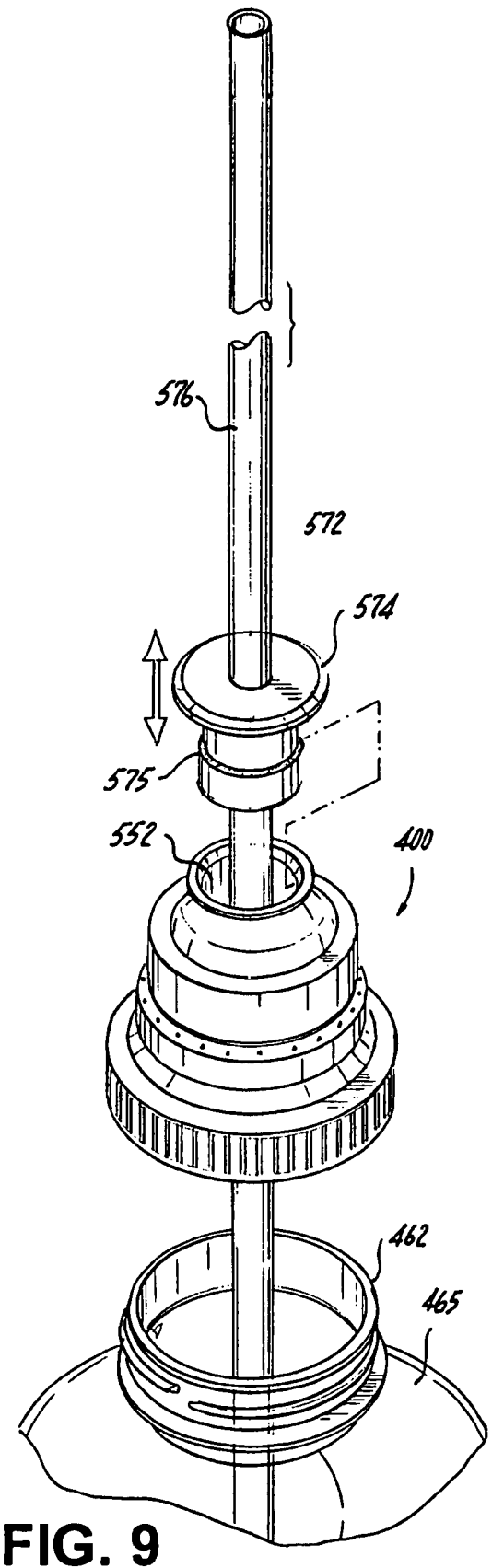
FIG. 8     FIG. 9

FIG. 11
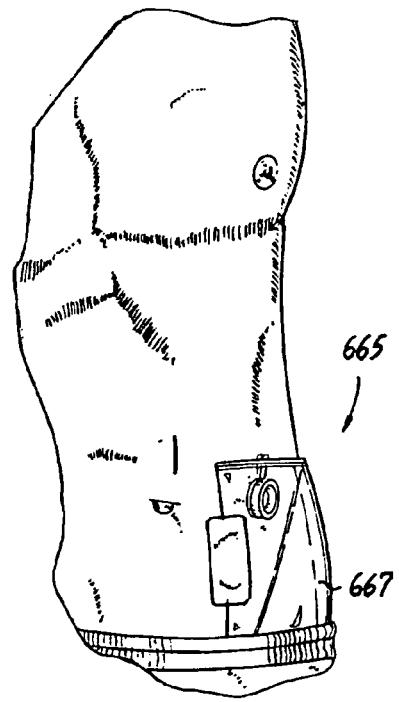
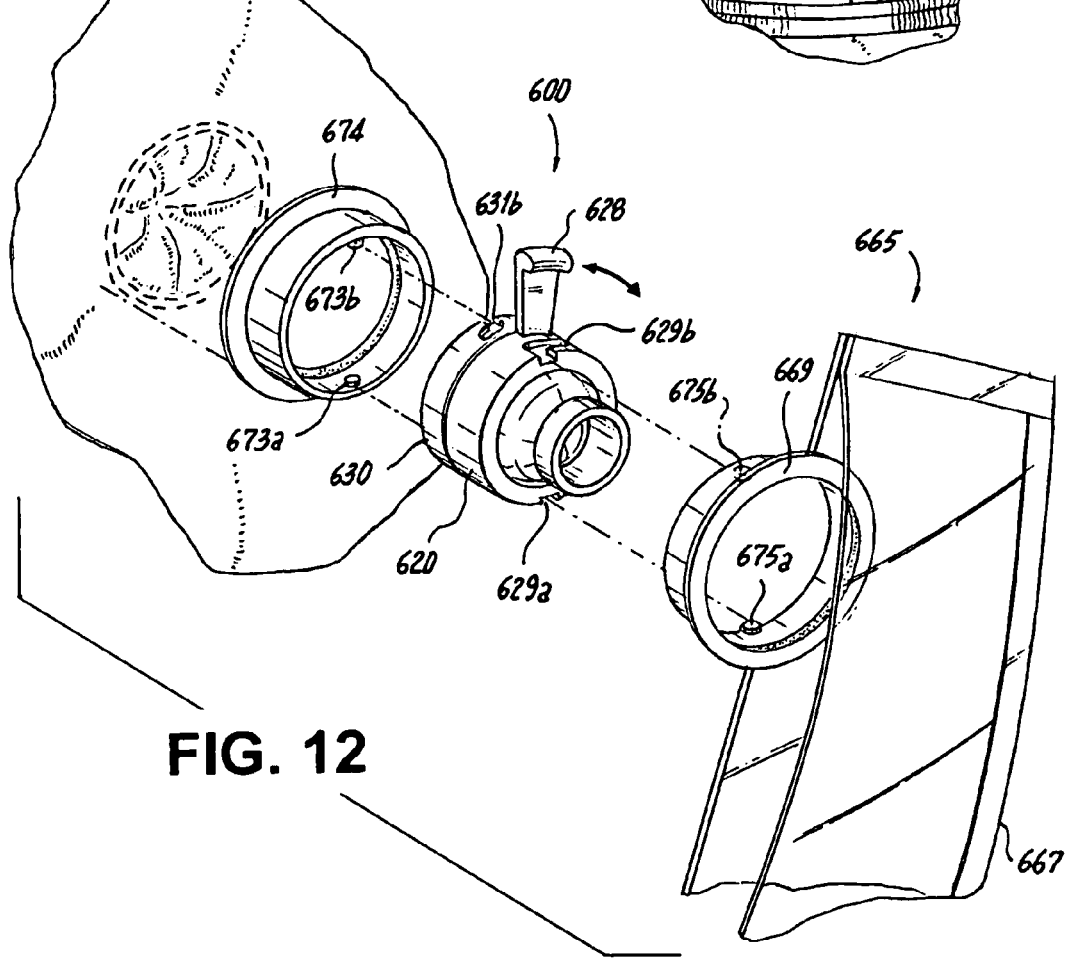
FIG. 12

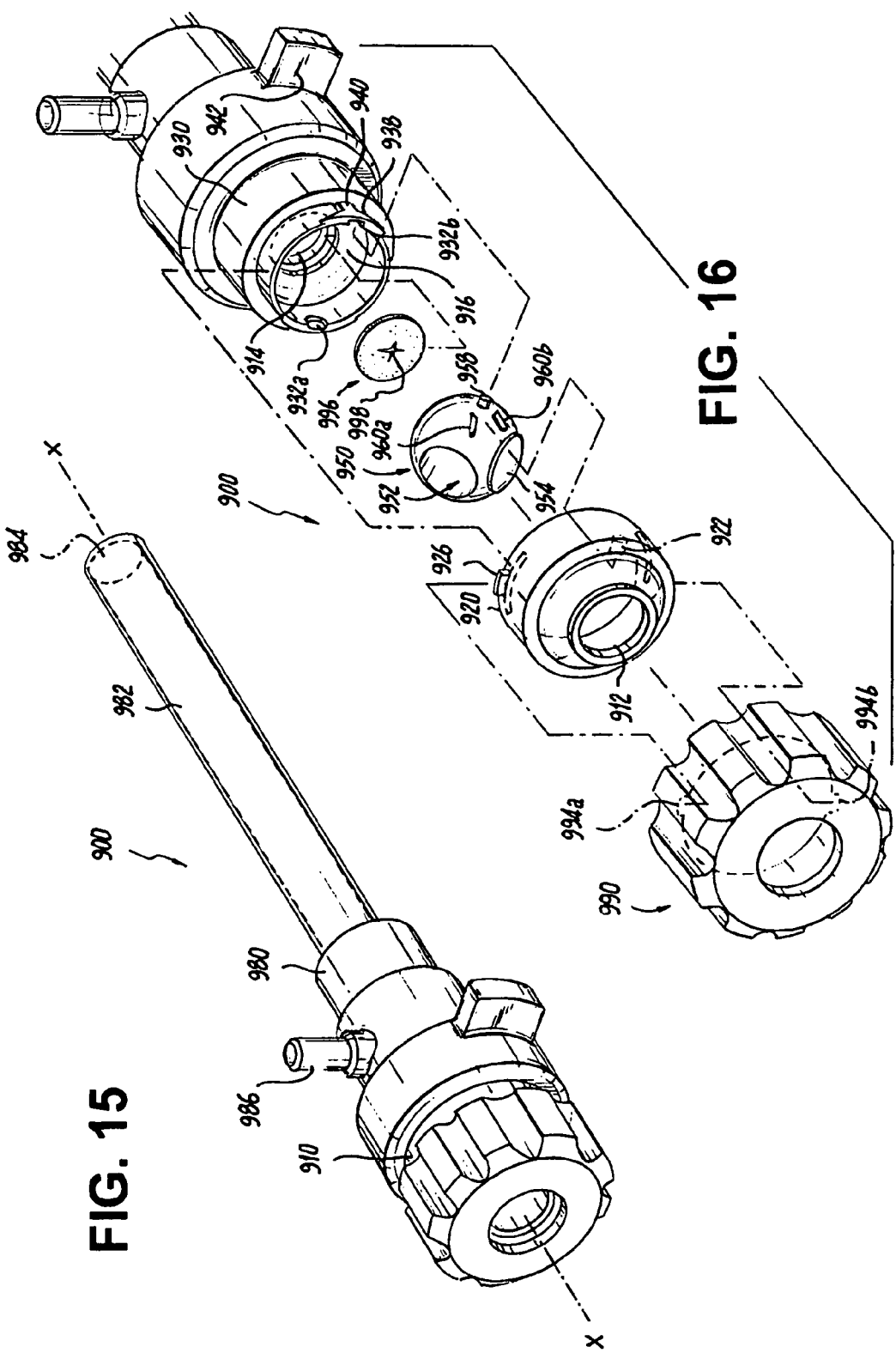

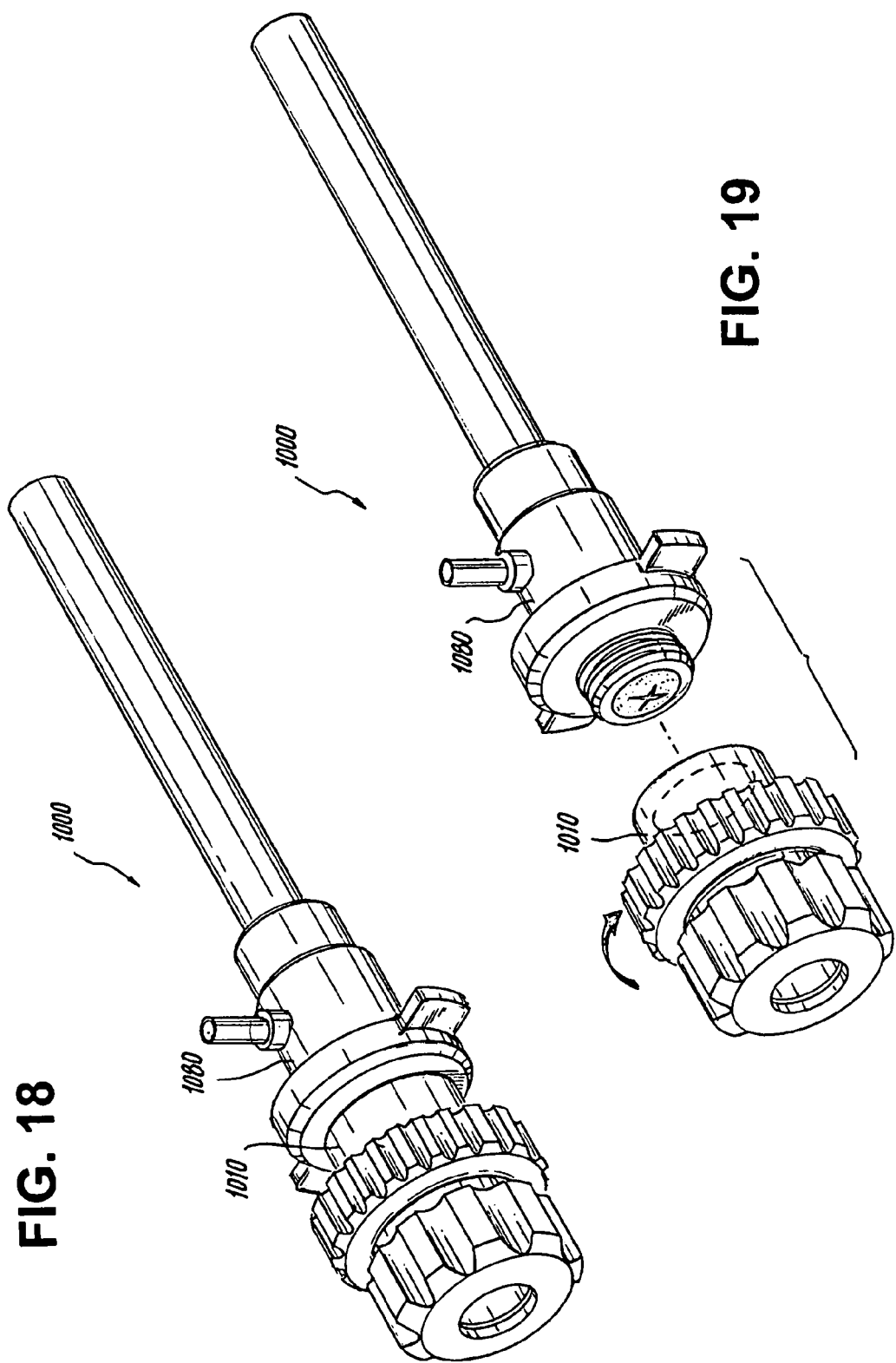

ROTATING VALVE ASSEMBLY

CROSS REFERENCE TO RELATED APPLICATIONS

This application claims priority to New Zealand Provisional Patent Application Serial No. 526158, filed May 29, 2003, entitled "Rotating Sealing Mechanism" and U.S. Provisional Patent Application Ser. No. 60/516,569, filed Oct. 31, 2003, entitled "Valve Assembly for Surgical Access Device", the disclosures of each are herein incorporated by reference in their entirety. This application is a continuation of U.S. patent application Ser. No. 10/856,011, filed May 28, 2004, now U.S. Pat. No. 7,165,568.

BACKGROUND OF THE INVENTION

1. Field of the Invention

The subject invention relates generally to the field of sealing mechanisms, and more particularly to, a compact valve assembly for use in a variety of applications, which includes a valve member that is readily actuated between the open and the closed position by a camming mechanism.

2. Background of the Related Art

Ball valves are well known to those skilled in the art and are commonly used in a variety of applications and industries. Typically, in applications that concern controlling the flow of a fluid, an apertured ball valve is selected. In an apertured ball valve, a generally spherical valve member that has a flow aperture or passage formed therethrough is positioned for rotational movement within a valve housing. The valve operation or function is broken down into two separate stages. First, the ball moves between an open and a closed position by rotating through 90 degrees, such that the aperture or flow passage moves from an orientation coaxial with the flow direction, i.e. when the valve is open, to a position whereby the ball aperture is normal or perpendicular to the flow direction. Second, the valve seals in the closed position to prevent flow through the aperture across the ball valve. Therefore, the on-off control of flow through the valve is achieved by rotating the ball through 90 degrees within the valve housing.

In prior art ball valves; the rotation of the ball (i.e., valve member) is typically effectuated by an actuator mechanism that protrudes from the valve housing and is configured to rotate about an axis perpendicular to that of the valve flow. Such a valve is disclosed in U.S. Pat. No. 6,695,285 to Hotton et al.

Several disadvantages are associated with this type of ball valve. For example, the extension of an actuator from the sidewall of the valve is cumbersome and not desirable for applications where space limitations and physical access to the actuator are a concern. Still further, the actuator in these valves must be rotated or turned through at least 90 degrees in order for the valve to move between the fully open and fully closed positions.

Therefore, it would be beneficial therefore, to provide a valve/seal mechanism that is compact, reliable and readily actuated between the open and closed position and actuated with a minimal amount of rotational movement.

SUMMARY OF THE INVENTION

The subject application is directed to a valve/seal assembly that is adapted for use in a variety of applications, such as for example, medical, consumer beverage, pharmaceutical containers, automobile, household appliance and marine. The disclosed valve includes, inter alia, a valve housing having an upper body portion and a lower body portion and a generally spherical valve member. The upper and lower body portions of the housing define an internal chamber for accommodating the valve member and a central axis for the valve. The housing also has axially aligned inlet and outlet ports formed in the upper and lower body portions, respectively.

The generally spherical valve member is seated within the internal chamber of the valve housing and has an axial bore extending therethrough. The valve member is mounted for movement between an open position; wherein the axial bore of the valve member is axially aligned with the inlet and outlet ports of the valve housing, and a closed position; wherein the axial bore of the valve member is out of alignment with the inlet and outlet ports of the valve housing. Preferably, the valve member moves between the open position and the closed position when the upper body portion of the housing is rotated about the central axis between about 57 degrees and about 77 degrees with respect to the lower body portion. It is presently envisioned that the valve member is mounted for axial rotation within the interior chamber about an axis extending perpendicular to the central axis defined by the upper and lower body portion of the valve housing.

Preferably, the valve member includes a sealing surface adapted for sealing engagement with a valve seat formed in the housing when the valve is in the closed position. In applications where a pressure is applied to the fluid or air metered by the valve, the sealing surface of the valve member is adapted to include an annular recess having an o-ring disposed therein.

The valve assembly further includes a mechanism that is operatively associated with the valve housing and the valve member for moving the valve member between the open position and the closed position when the upper body portion of the housing is rotated about the central axis with respect to the lower body portion. In a preferred embodiment, the mechanism for actuating the valve assembly is a camming mechanism.

In a present embodiment, the camming mechanism includes cam surfaces formed on the exterior surface of the valve member and a cam pin formed on the interior surface of the upper body portion of the housing. It is envisioned that the cam surfaces formed on the exterior surface of the valve member are defined by a pair of cam lobes formed at angles to one another. The cam lobes can be arcuate or linear in configuration.

In a further embodiment of the present invention, the camming mechanism includes at least one arcuate recess formed on the exterior surface of the valve member and a cam pin formed on the interior surface of the upper body portion of the housing for engaging with the cam recess.

In a preferred embodiment, the housing for the valve assembly includes means associated with the inlet port for engaging the valve with a receptacle or tubing. Additionally, if desired, the housing can includes means associated with the outlet port for engaging the valve with a receptacle or tubing.

In applications that require the valve to include a tamper-proof feature to ensure the purity of the substance contained within the bore of the valve member or in the receptacle or container, upon which the valve is affixed to, the valve further includes a frangible ring engaged with exterior of the valve housing to provide a visual indication of whether the valve has been opened. Alternatively or in combination, the valve can include a frangible sealing disc inserted into the interior chamber of the valve to again provide a visual indication of whether the valve has been opened. This sealing disc also functions as a secondary seal for the valve until its initial use. In this embodiment, it is envisioned that the valve member includes a mechanism for puncturing the disc when the valve is opened. For example, a sharp protuberance can be formed on the bottom of the valve member which cuts the sealing disc when the valve is moved from the closed to the open position.

In an alternative embodiment, the axial bore of the valve member is adapted and configured for receiving and storing an article of manufacture when the valve is in the closed position. For example, an award or small prize may be stored in the bore and revealed when the valve is opened. Still further, the valve could be mounted to a water bottle and the bore of the valve could contain a vitamin or supplement which is dropped into the water when the valve is opened.

It is further envisioned that the valve can include a mechanism associated with the valve housing for facilitating the axial rotation of the upper body portion of the housing relative to the lower body portion.

In an alternative embodiment, a plurality of flow passages are formed in the valve member and extend therethrough along an axis that is perpendicular to the axial bore such that when the valve is in the closed position, fluid or air traverses the valve through the plurality of flow passages.

The present disclosure is also directed to a surgical access device which includes, among other things, a valve housing, an elongated cannula sleeve operatively associated with the housing, a generally spherical valve member disposed within an interior chamber defined in the housing and a mechanism operatively associated with the valve housing and the valve member for moving the valve member between the open position and the closed position.

The valve housing defines an interior chamber and a valve seat for accommodating the valve member. Axially aligned inlet and outlet ports are formed in the housing and extend from the valve exterior to the interior chamber.

The elongated cannula sleeve that is operatively associated with the valve housing, has an elongated passageway extending therethrough that defines a longitudinal axis aligned with the inlet and outlet ports of the valve housing. In a disclosed embodiment, the cannula sleeve depends from a cannula housing associated with the valve housing. It is envisioned that the cannula housing can be detachably connected to the valve housing.

The generally spherical valve member is seated within the valve housing and has an axial bore extending therethrough. The valve member is mount ed for movement between an open position and a closed position. In the open position, the axial bore of the valve member is axially aligned with the elongated passageway of the cannula sleeve and the inlet and outlet ports of the valve housing. In the closed position, the axial bore of the valve member extends perpendicular to the elongated passageway of the cannula sleeve and the inlet and outlet ports of the valve housing. It is envisioned that the valve member is mounted for axial rotation within the valve interior chamber about an axis extending perpendicular to the axially aligned inlet and outlet ports of the valve housing.

It is presently envisioned that the valve member includes a convex sealing surface, which is aligned with the inlet port of the valve housing when the valve member is in the closed position. In alternative embodiments that require a pressure tight seal, the sealing surface of the valve member includes an annular recess having an o-ring disposed therein.

In a preferred embodiment, the mechanism for moving the valve member includes cam surfaces formed on the exterior surface of the valve member and a cam pin mounted for movement relative to the cam surfaces of the valve member. Preferably, the cam pin extends radially inwardly from a drive ring supported on the valve housing and mounted for rotation about the longitudinal axis of the cannula sleeve. The rotation of the drive ring causes corresponding rotation of the valve member within the valve seat of the valve housing.

In a disclosed embodiment of the surgical access device, the cam surfaces formed on the exterior surface of the valve member are defined by a pair of cam lobes oriented with respect to the axis of rotation of the valve member at angles to one another.

In an alternative embodiment, the mechanism operatively associated with the valve housing and the valve member for moving the valve member between the open position and the closed position includes at least one arcuate recess formed on the exterior surface of the valve member and a cam pin formed on the interior surface of the housing for engaging with the cam recess.

It is presently preferred that the surgical access device further includes a membrane seal located proximal to the valve seat, the membrane seal having an opening axially aligned with the elongated passageway of the cannula sleeve. The opening is dimensioned to accommodate the passage of a surgical instrument therethrough.

Those skilled in the art would readily appreciate that the components of the disclosed valve assembly, or portions thereof, may be manufactured from any rigid, semi-rigid, hard or semi-hard material, such as plastic, rubber, metal or a composite. Still further, in medical applications the valve assembly can be made out of titanium or a similar biocompatible material.

Additionally, the generally spherical valve member can be formed to have an interference fit with the valve seat so as to provide a tighter seal. By forming the valve member or valve seat slightly out-of-round, a tighter seal is created and more force is required to open the valve.

It is also envisioned that a telescoping nozzle or sleeve can be disposed within the axial bore of the valve member and when the valve is moved to the open position, the nozzle or sleeve extends out of the valve inlet. This feature is useful in a variety of applications, such as for example, beverage or gasoline containers.

Still further, it is envisioned that the valve assembly of the present invention can be connected to stepper motor and thereby be operated remotely.

BRIEF DESCRIPTION OF THE DRAWINGS

So that those having ordinary skill in the art to which the present application appertains will more readily understand how to make and use the surgical access device and valve assembly of the present invention, embodiments thereof will be described in detail hereinbelow with reference to the drawings, wherein:

FIG. 8 is a perspective view of a valve assembly constructed in accordance with a further alternative embodiment of the subject invention, wherein the valve assembly is mounted on the end of a tubing which is in fluid communication with a container;

FIG. 9 is a perspective view of a valve assembly constructed in accordance with a further alternative embodiment of the subject invention, wherein the valve assembly is mounted on a container and a straw assembly is position within the open valve;

FIG. 11 is a perspective view of the valve assembly of the present disclosure adapted for use with a colostomy bag;

FIG. 12 is a perspective view of the valve assembly of FIG. 11 with parts separated for ease of illustration;

FIG. 15 is a perspective view of a surgical access dev ice constructed in accordance with a preferred embodiment of the subject invention;

FIG. 16 is an exploded perspective view of the surgical access device of FIG. 15 with parts separated for ease of illustration;

FIG. 18 is a perspective view of another embodiment of the surgical access device of the subject invention, which includes a detachable valve housing; and FIG. 19 is a perspective view of the surgical access device of FIG. 18, with the valve housing separated from the cannula housing for ease of illustration.

These and other features of the valve assembly and surgical access device of the present application will become more readily apparent to those having ordinary skill in the art form the following detailed description of the preferred embodiments.

DETAILED DESCRIPTION OF PREFERRED EMBODIMENTS

Figure 1:
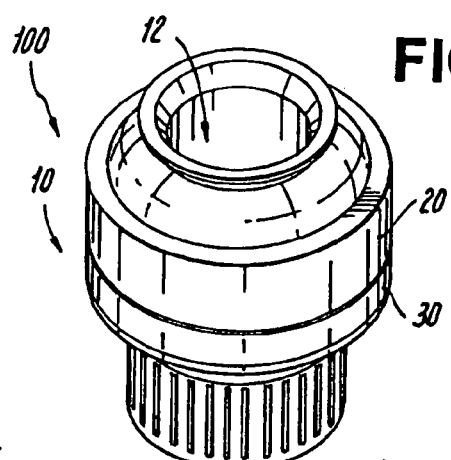
FIG. 1 is a perspective view of a valve assembly constructed in accordance with a preferred embodiment of the subject invention.

Referring now to the drawings wherein like reference numerals identify similar structural elements or features of the subject invention, there is illustrated in FIG. 1 a valve assembly in accordance with the present invention and designated generally by reference number 100. Valve assembly 100 is adapted for use in a variety of applications, such as for example, medical, consumer beverage, pharmaceutical containers, automobile, household appliance and marine. Valve 100 includes, inter alia, a valve housing 10 having an upper body portion 20 and a lower body portion 30 and a generally spherical valve member 50. The upper and lower body portions 20/30 of the housing 10 define an internal chamber 16 for accommodating the valve member 50 and a central axis "X" for the valve. The housing 10 also has axially aligned inlet and outlet ports, 12 and 14 respectively, formed in the upper and lower body portions, 20 and 30 respectively.

Figure 3A:
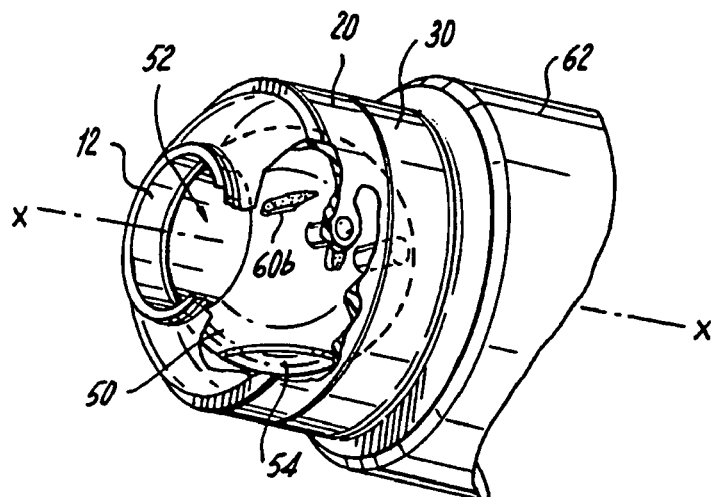
Figure 3B:
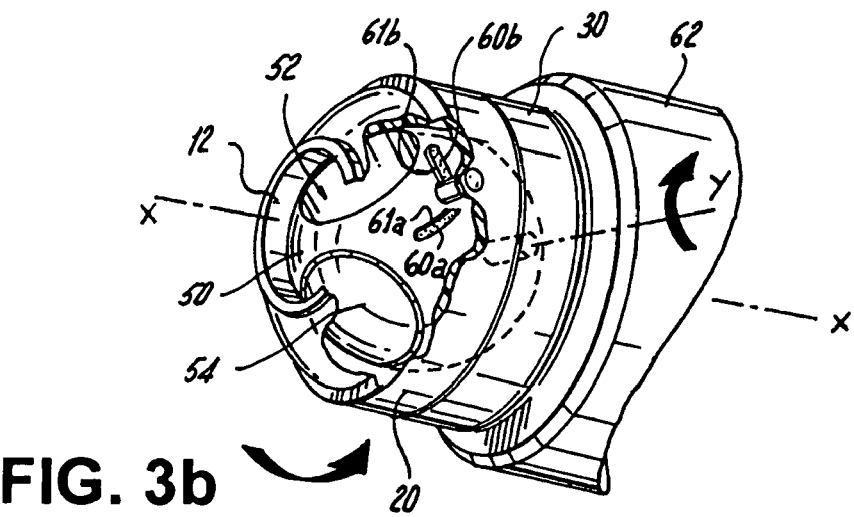
Figure 3C:
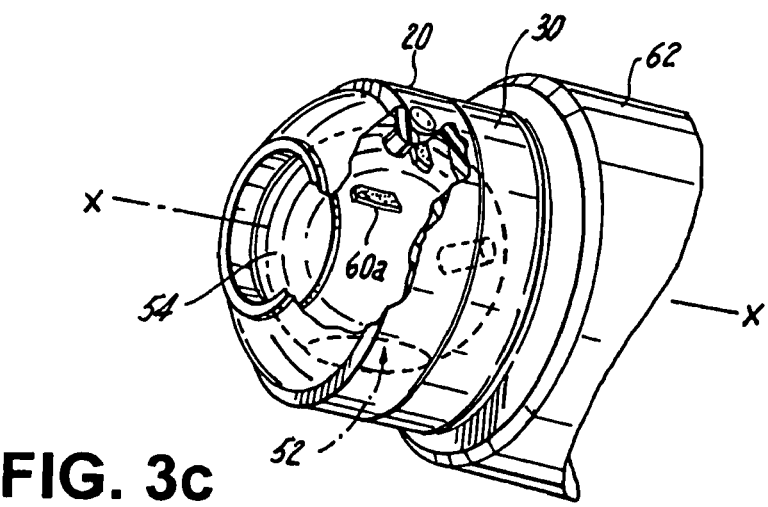

The generally spherical valve member 50 is seated within the internal chamber 16 of the valve housing and has an axial bore 52 extending therethrough. The valve member 50 is mounted for movement within the internal chamber 16 of the housing 10 between an open position and a closed position. FIG. 3a illustrates valve assembly 100 in the open position; wherein the axial bore 52 of the valve member 50 is axially aligned with the inlet port 12 and outlet port 14 of the valve housing 10. In a like manner, FIG. 3c illustrates the valve assembly 100 in the closed position; wherein the axial bore 52 of the valve member 50 is out of alignment with the inlet and outlet ports 12/16 of the valve housing 10. FIG. 3b, provides a detail of the valve assembly 100 in an intermediate position. It should be noted that in FIGS. 3a through 3c, valve assembly 100 is shown mounted on the neck of a container 62.

With continuing reference to FIGS. 3a through 3c, valve member 100 moves between the open position and the closed position when the upper body portion 20 of the housing is rotated about the central axis "X" between about 57 degrees and about 77 degrees with respect to the lower body portion 30. The valve member 50 is mounted for axial rotation within the interior chamber about an axis "Y" (see FIG. 3b) extending perpendicular to the central axis "X" defined by the upper and lower body portions 20/30 of the valve housing 10.

The valve member 50 includes a sealing surface 54 which is adapted for sealing engagement with annular valve seat 18 formed in the housing 10 when the valve is in the closed position. In applications where a pressure is applied to the fluid or air that is metered by the valve assembly, the sealing surface 54 of the valve member 50 includes an annular recess 56 (see FIG. 2) having an o-ring (not shown) disposed therein.

Figures 2, 3:
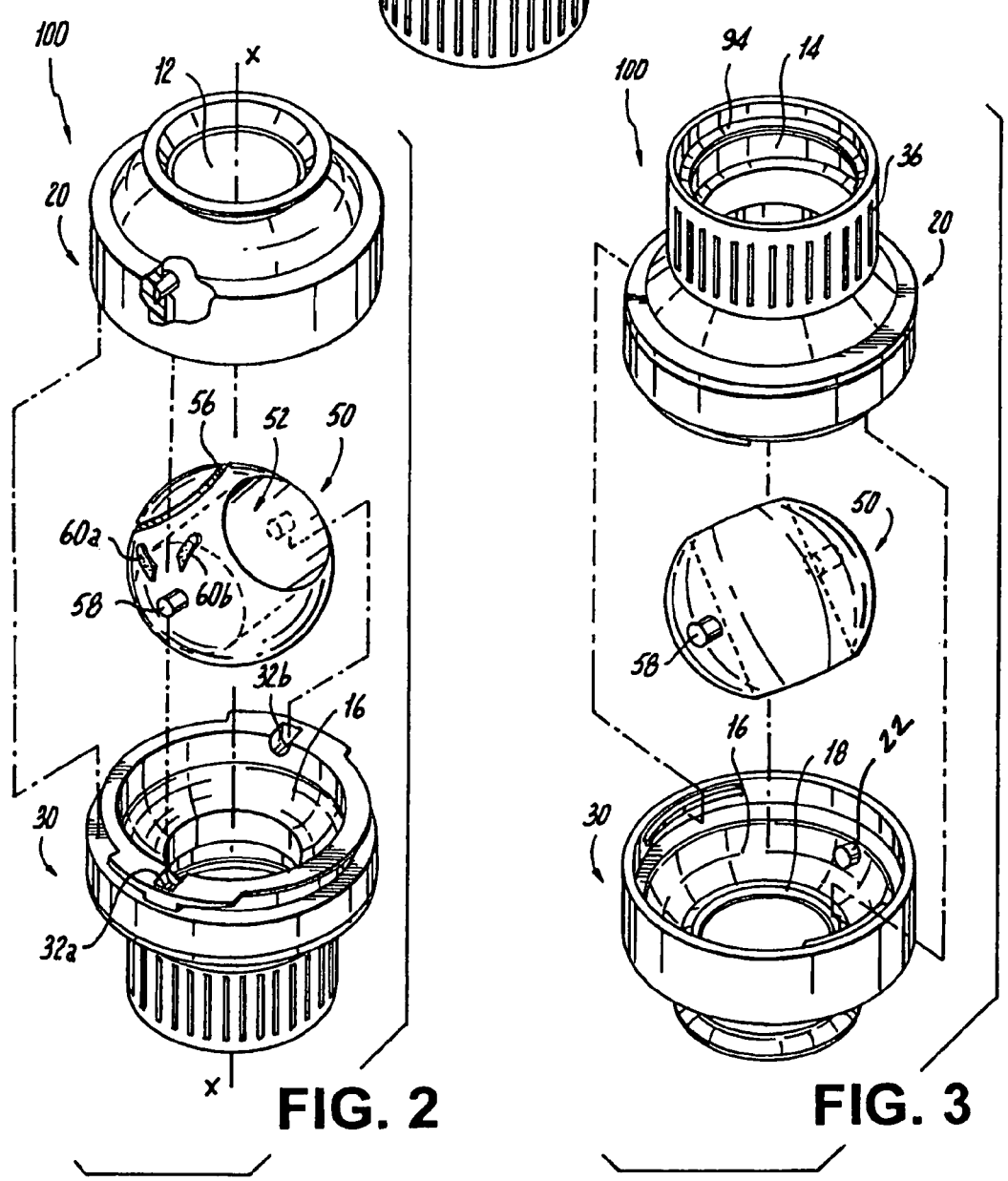
FIG. 2 is an exploded perspective view from above of the valve assembly of FIG. 1 with parts separated for ease of illustration.
FIG. 3 is an exploded perspective view from below of the valve assembly of FIG. 1 with parts separated for ease of illustration.

Diametrically opposed pivot pins 58 (only one pin is shown in FIG. 2) extend radially outwardly from the surface of valve member 50 for accommodation within diametrically opposed recesses 32a and 32 formed in the lower body portion 30 of the housing 10 to facilitate the axial rotation of valve member 50.

A camming mechanism is operatively associated with the valve housing 10 and the valve member 50 for moving the valve member 50 between the open position of FIG. 3a and the closed position of FIG. 3c. The camming mechanism includes cam lobes 60a, 60b formed on the exterior surface of the valve member 50 and a cam pin 22 which extends radially inwardly from the interior surface of the upper body portion 20 of the housing 10 to cooperate with the cam lobes. As will be described in detail herein below, the valve assembly can be equipped with a drive ring which is engaged over the upper body portion of the housing. In such an embodiment, the cam pin can be associated with the drive ring such that the drive ring actuates the valve member.

Referring again to FIG. 3b, the cam lobes 60a, 60b are oriented with respect to the axis of rotation "Y" of the valve member 50 at angles to one another. Each cam lobe 60a, 60b has a leading edge 61a, 61b that interacts with the cam pin 22. This interaction facilitates movement of the valve member 50 when the upper body portion 20 is rotated about the longitudinal axis X of the valve assembly 100. When the valve member 50 is moved between the open and closed positions, it is rotated about the pivot axis "Y" which extends through the pivot pin 58 of valve member 50, as illustrated in FIG. 3b.

Those skilled in the art would readily appreciate that in lieu of the cam lobes 60a and 60b, a single arcuate recess or pair of recesses can be formed in the exterior surface of valve member 50. In this embodiment, the length of cam pin 22 would be selected so that it extends into the camming recess (es) and actuates the valve member 50 between the open and closed positions upon the relative axial rotation of the two body portions 20/30 of the housing 10 with respect to each other.

Referring again to FIGS. 2 and 3, the lower body portion 30 of valve assembly 100 has a female thread series 34 formed thereon for engaging with corresponding male series associated with a receptacle (e.g. bottle, container, etc.), tubing or the like. Ribbed surface 36 is provided on the exterior of the lower body portion 30 of the housing 10 to facilitate the rotational engagement of the threads.

A water pressure test was conducted on a valve assembly similar to that described above. The entire valve was manufactured from a rigid theremoplastic and did not include O-ring seals. The camming lobes were constructed such that 67 degrees of rotation was required to move the valve between the open and the closed position. The axial bore of the valve was approximately ¾" in diameter. Six feet of water was applied to the valve through a ⅜" tube that was secured to the valve outlet. No leaking of the valve was observed and therefore, it was concluded that this embodiment of the valve assembly was capable of sealing fluid at a pressure of 3 psi (minimum).

Figures 4, 5:
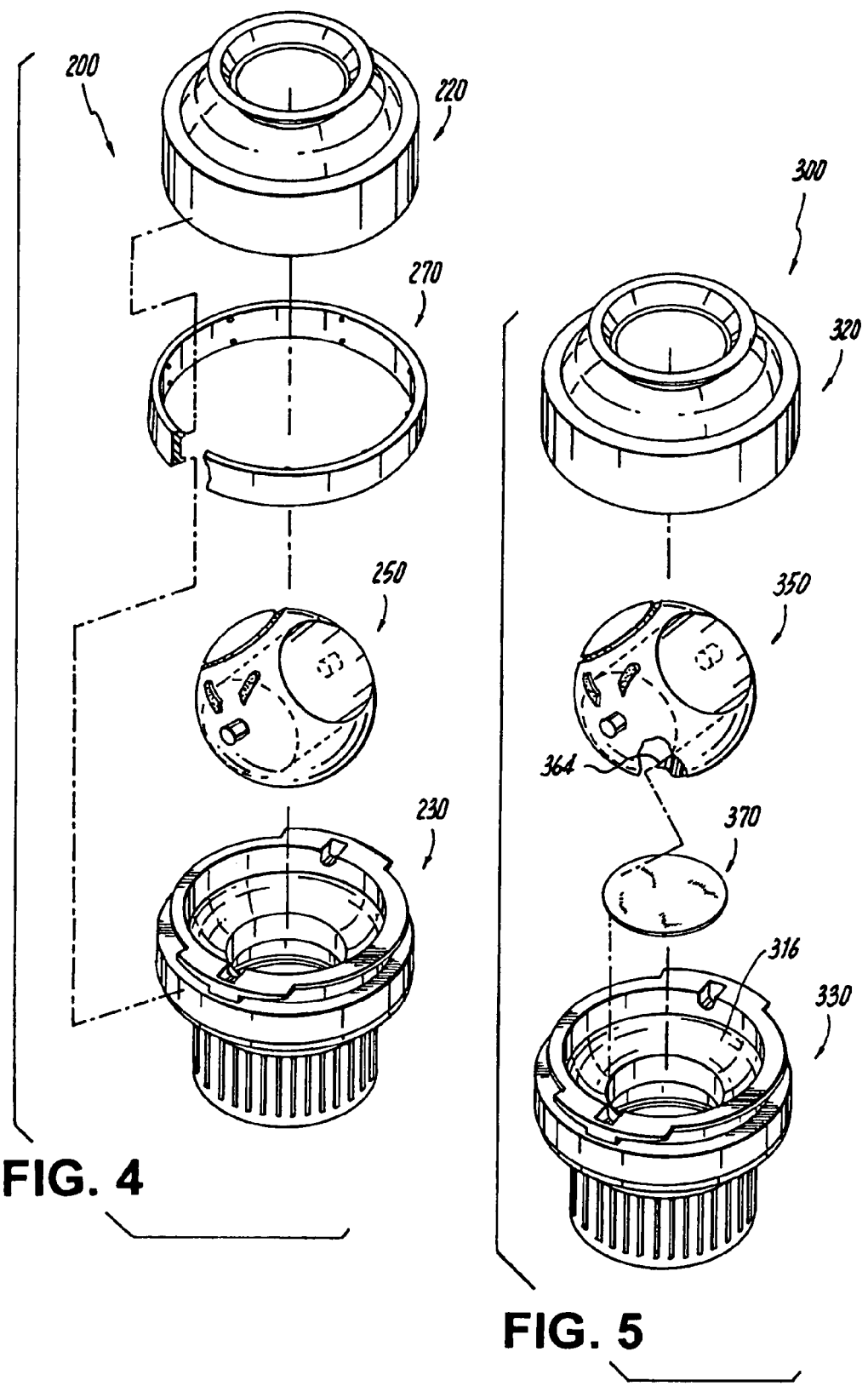
FIG. 4 is an exploded perspective view of an alternative embodiment of the valve assembly of the present invention with parts separated for ease of illustration, wherein the valve includes a frangible ring.
FIG. 5 is an exploded perspective view of an alternative embodiment of the valve assembly of the present invention with parts separated for ease of illustration, wherein the valve includes a sealing disc disposed within the interior chamber of the housing.

Referring now to FIG. 4, there is illustrated an alternative embodiment of the valve assembly of the present invention designated generally by reference numeral 200. Valve 200 is similar in structure and operation to valve assembly 100. However, unlike valve assembly 100, valve assembly 200 includes a frangible ring 270 which is adapted to be engaged with the housing (i.e., the upper and lower body portions 220, 230) of the valve assembly 200. The frangible ring 270 has been added to valve assembly 200 to provide a visual indication of whether the valve has been previously opened. Frangible ring 270 is molded around the upper and lower body portions 220, 230 of the housing so that when the body portions are rotated relative to each of the, the ring 270 is broken. Such a tamper-proof feature would be useful in applications where the valve is with consumer beverages, for example.

Referring now to FIG. 5 which illustrates a further embodiment of the valve assembly of the present invention that has been designated by reference number 300. Valve 300 is similar in structure and operation to valve assembly 100. However, unlike valve 100, valve 300 includes a frangible sealing disc 370 which is positioned within the interior chamber 316 defined in part by the lower body portion of the housing. Frangible sealing disc 370 can function as a tamper-proof feature, as well as, provide an additional seal for valve assembly 300. In this embodiment, the valve member 350 has a shape protuberance 364 formed on its exterior surface. When the valve member 350 is rotated from the open to the closed position the protuberance 364 punctures the sealing disc 370 allowing fluid or air to flow through the valve member 350 when it is returned to the closed position.

Figure 6:
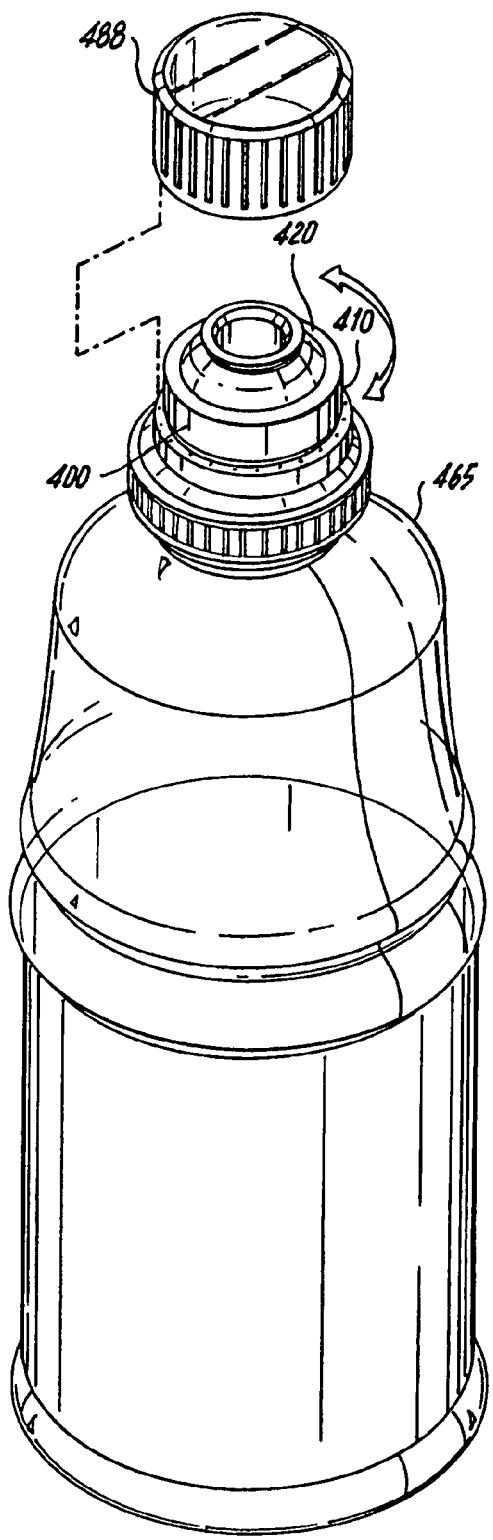
FIG. 6 is a perspective view of a valve assembly constructed in accordance with an alternative embodiment of the subject invention, wherein the valve assembly is engaged with a beverage container and is adapted for engagement with a cap.
Figure 7:
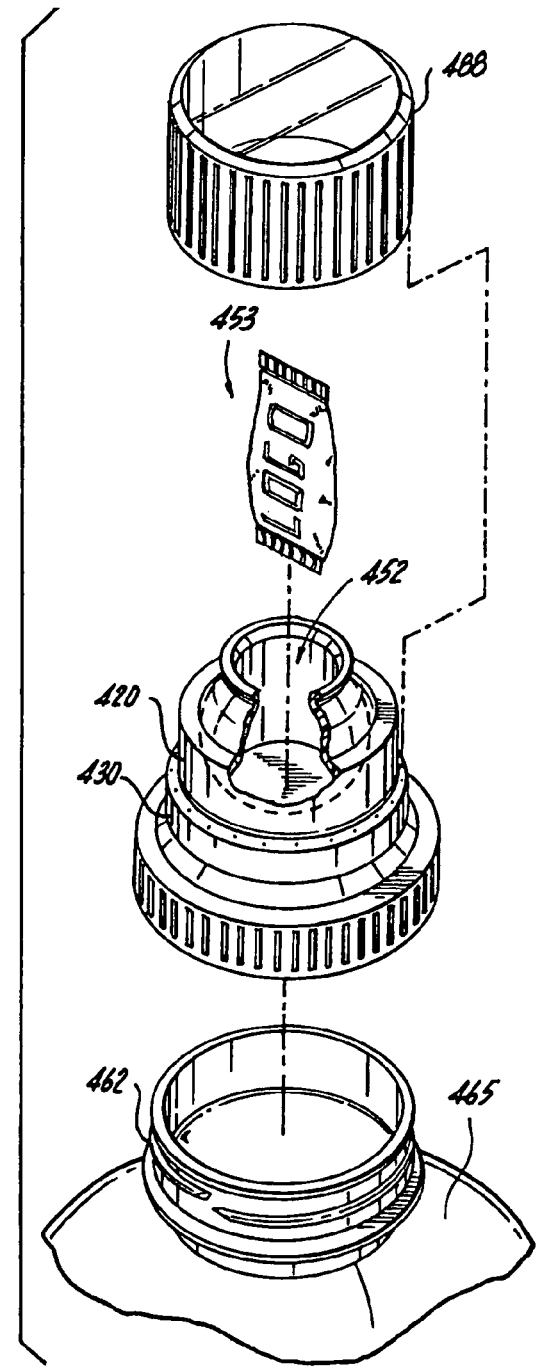
FIG. 7 is a perspective view of a valve assembly constructed in accordance with an alternative embodiment of the subject invention with parts separated for ease of illustration, wherein a prize is stored within the bore formed in the valve member.

Referring now to FIGS. 6 and 7, which illustrate yet another embodiment of the valve assembly of the present invention designated generally by reference numeral 400. Valve assembly 400 is similar in structure and operation to valve assembly 100. As shown in these figures, valve assembly 400 is threadably engaged with the neck 462 of container 465. A cap 488 is provided which engages with the upper portion 420 of the valve assembly 400. Like the previously disclosed valve assemblies, valve member 450 has a axial bore 452 formed therein which allows fluid or air to flow through the valve assembly 400 when the valve member 450 is in the open position. Still further, the axial bore 452 is adapted for receiving and storing an article of manufacture 453 or fluid, such as for example, a prize, a ticket, a vitamin supplement, or a medication. In such embodiments, it would be advantageous to insert a sealing disc into the valve assembly similar that disclosed with reference to FIG. 5 to prevent to article of manufacture from falling into the container during storage. Alternatively, a removable seal can be placed over the mouth of container 462.

Referring now to FIGS. 8 and 9 which illustrate an alternate application for valve 400. In FIG. 8, valve 400 is mounted on the end of a tubing assembly 472. Tubing assembly 472 includes two end connectors 474a, 474b and an elongated tube 476. End connector 474a is threadably engaged with the neck of container 465 and includes a central aperture which is adapted to allow tube 476 to telescope in and out of container 465. Valve assembly 400 is engaged with end connector 474b such that when the valve is in the open position, fluid can flow from the container 465 through the tubing assembly 472 and out of the valve 400.

FIG. 9 illustrates valve assembly 400 mounted on the neck 462 of container 465. Valve assembly 400 is shown in the open position having straw assembly 572 inserted into the axial bore 552. Straw assembly 572 includes a straw 576 and a plug member 574. The plug member 574 has a circumferential O-ring 575 and is adapted for sealing engagement with the inlet port of valve 400.

Figure 10:
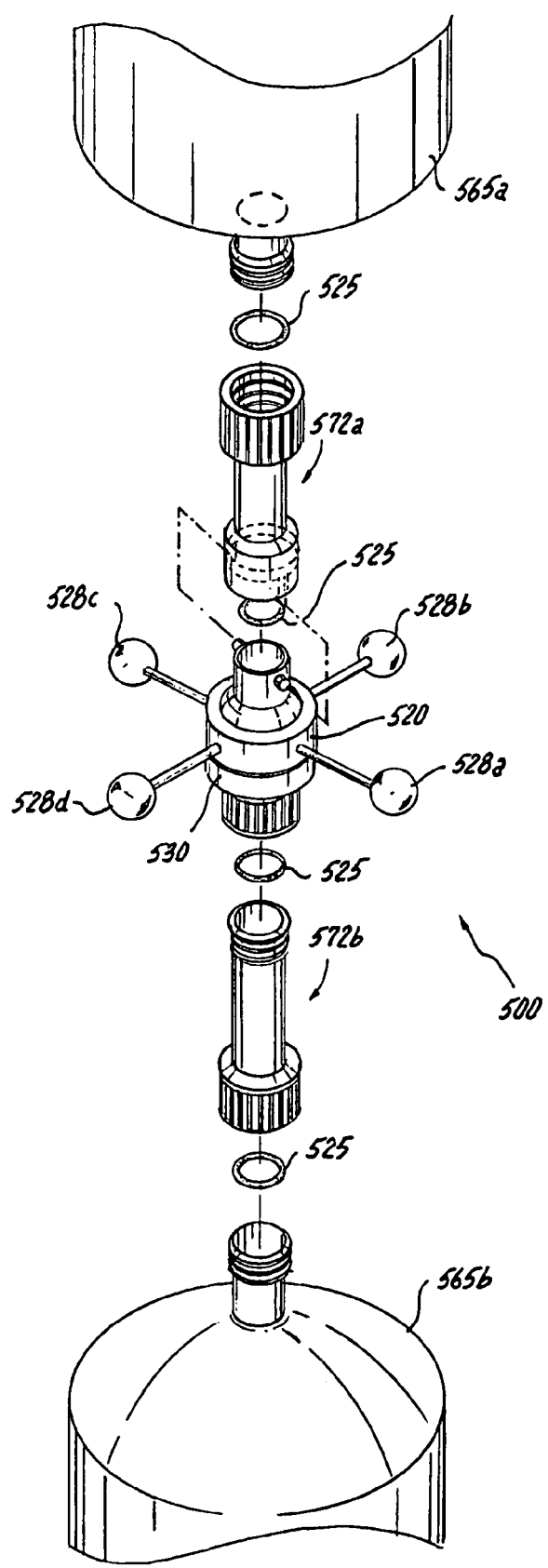
FIG. 10 is a perspective view of the valve assembly of the present disclosure which illustrates the valve positioned between two containers.

Referring now to FIG. 10, which illustrates a further embodiment of the valve assembly of the present invention, designated generally by reference numeral 500. As shown herein, valve assembly 500 is being used to meter the flow between two containers 565a, 565b. The flow path between the containers includes upper and lower conduit assemblies 572a, 572b and valve assembly 500. The conduit assemblies are sealingly engaged between containers 565a, 565b and the valve assembly 500.

Valve assembly 500 is similar in structure and function to valve assembly 100. However, unlike valve assembly 100, valve assembly 500 includes actuator arms 528a through 528d that facilitate the relative rotation of the upper body portion 520 of the valve assembly 500 with respect to the lower body portion 530 thereby moving the valve member between the open and closed positions. O-rings 525 are provided to seal the connections of the components and prevent leakage from the flow path.

Referring now to FIGS. 11 and 12, wherein valve assembly 600 is shown used in conjunction with a colostomy bag assembly 665. Colostomy bag assembly 665, includes a bag 667, a proximal ring 669 and a distal ring 671. The proximal ring 669 has an outer flange that is sealingly engaged with the bag 667. Two retaining pins 675a, 675b are formed on the inside diameter of the proximal ring 669. These pins 675a, 675b are inserted into corresponding engagement recesses 629a, 629b formed in valve assembly 600 and secure the valve assembly 600 to the proximal ring 669. Similarly, distal ring 671, which is secured to the surface of the patient's body, includes retaining pins 673a, 673b that are inserted into corresponding engagement recesses 631a (not shown), 631b formed in valve assembly 600. Valve assembly 600 has been equipped with an actuator arm 628 which allows the patient to move the valve between the open and the closed position as desired.

Figure 13:
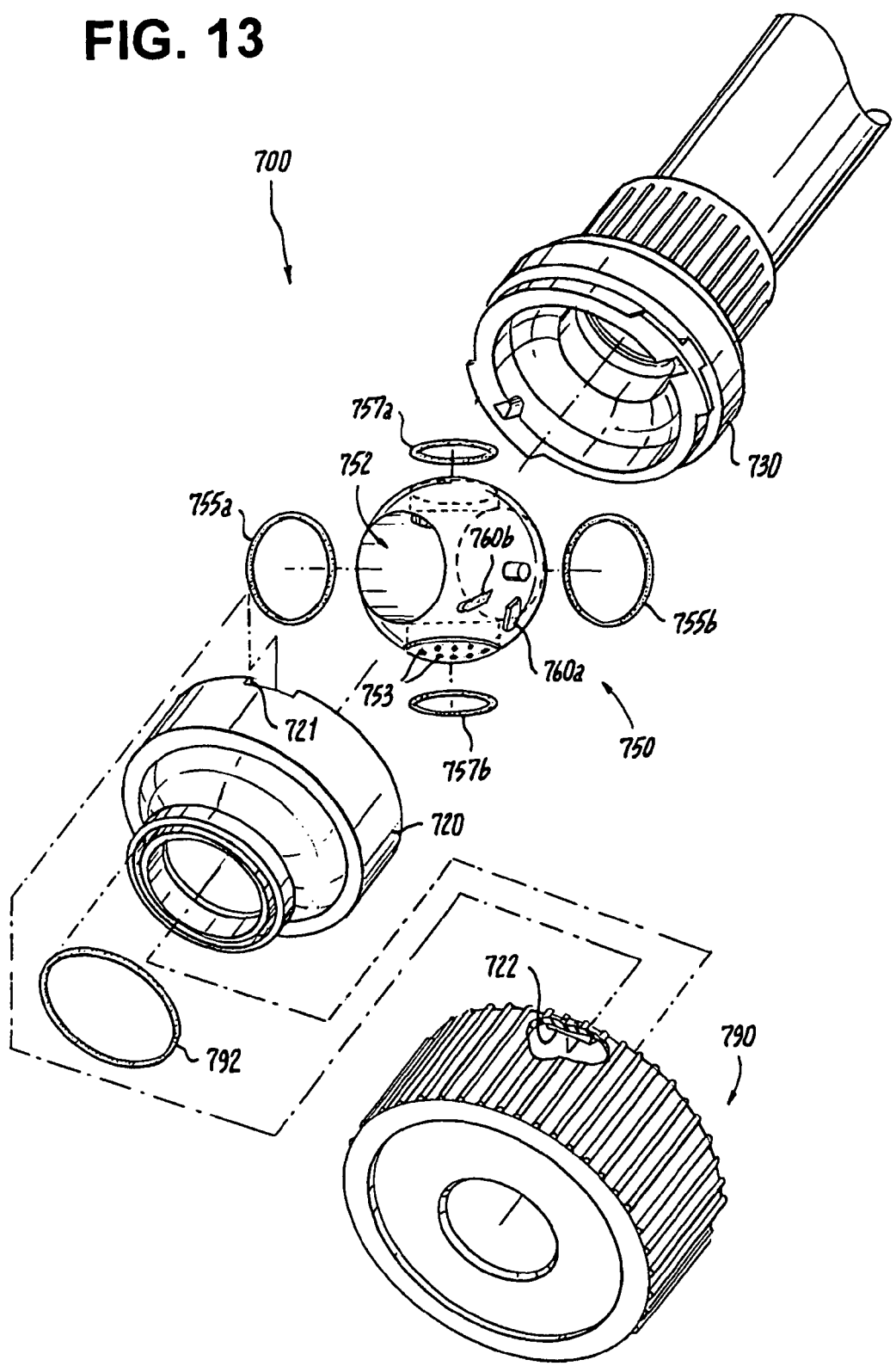
FIG. 13 is an exploded perspective view of an alternative embodiment of the presently disclosed valve assembly with parts separated for ease of illustration, wherein the valve member includes a plurality of flow passages extending through the valve perpendicular to the central bore.

Referring now to FIG. 13, there is illustrated a showerhead which includes a valve assembly constructed in accordance with an alternative embodiment of the present invention and designated by reference number 700. Again, valve assembly 700 is similar in structure and operation to the previously disclosed valves, but unlike the prior valves, valve assembly 700 has a plurality of flow passages 753 formed in the valve member 750.

The flow passages 753 extend along an axis that is perpendicular to the axial bore 752 such that when the valve member is in the closed position, fluid traverses the valve through the plurality of flow passages 753. Hence when the valve assembly 700 is in the open position, a single jet of water is emitted from the showerhead assembly and when it is in the closed position, water streams from the flow passages 753. O-ring seals 755a, 755b and 757a, 757b are provided at both ends of the axial bore 752 and flow passages 753 to properly seal the valve when in the open and closed positions, respectively.

The showerhead disclosed in FIG. 13 is also equipped with a control ring 790 that sealingly engages with the upper portion 720 of the valve assembly 700 using O-ring seal 792. Control ring 790 has a drive pin 722 formed on its interior surface. Drive pin 722 projects through the slot 721 formed in the upper portion 720 of the valve assembly 700 and engages with the cam lobes 760a, 760b formed the valve member 750. Thus, rotation of the control ring 790 with respect to the lower body portion 730 of the valve assembly 700 moves the valve member between the open and the closed positions.

Those skilled in the art will readily appreciate that the showerhead assembly described hereinabove can be adapted for use for metering an air supply rather than fluid.

Figure 14:
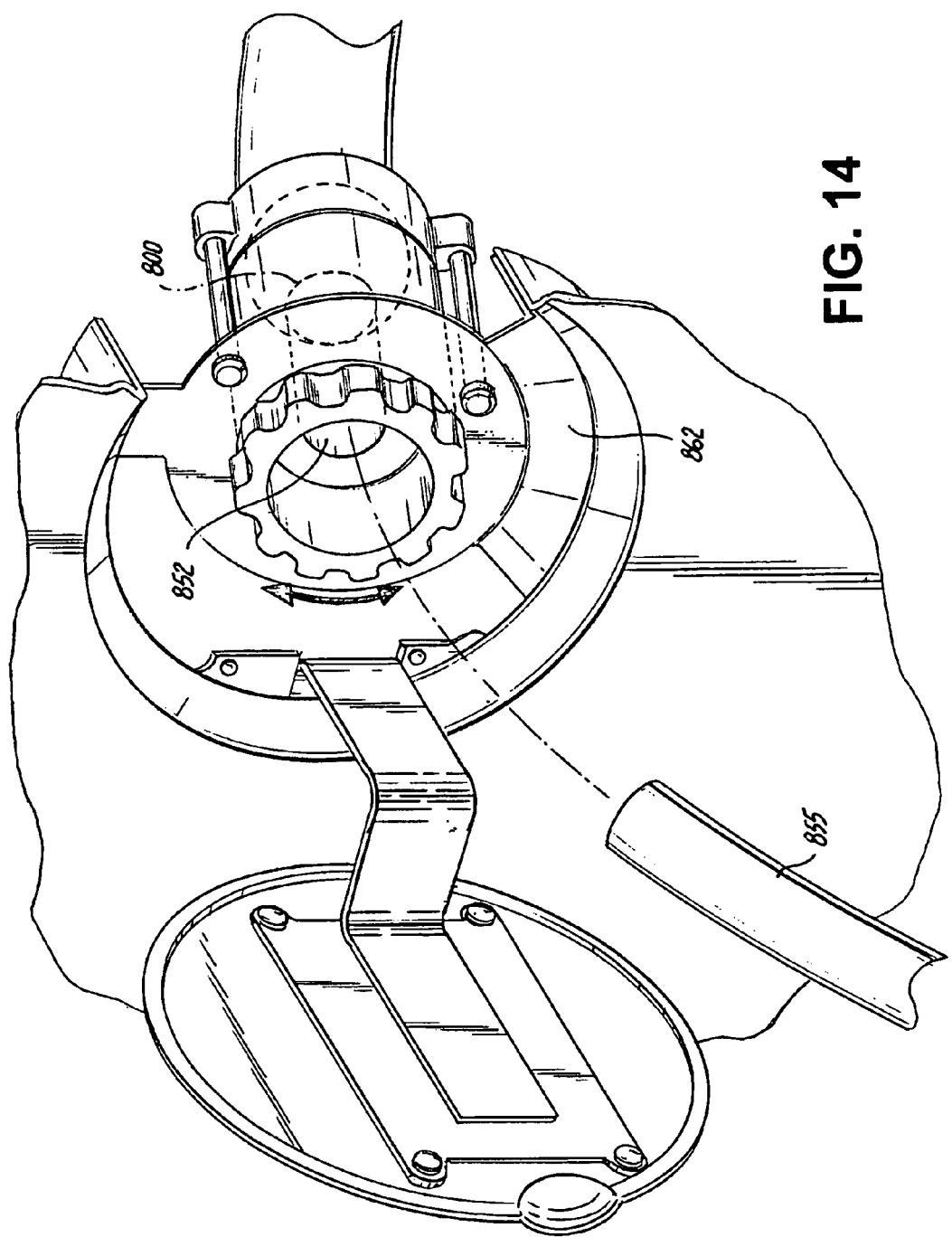
FIG. 14 is a perspective view of an alternative application for the valve assembly of the present invention, wherein the valve is used in a automobile fuel tank.

Referring now to FIG. 14 which illustrates a valve assembly (designated by reference numeral 800) constructed in accordance with the present invention positioned within the inlet 862 of fuel tank. The use of valve assembly 800 in this application allows for the elimination of a removable gas cap and only requires an approximately 67 degrees rotation of drive ring 890 to open the valve. The axial bore 852 of the valve member would be adapted for receiving a standard fuel pump nozzle 855.

Referring now to FIGS. 15 and 16, there is illustrated a surgical instrument constructed in accordance with a preferred embodiment of the subject invention and designated generally by reference numeral 900.

Minimally invasive surgical procedures are commonly performed by passing surgical instruments through a narrow tube or cannula inserted through a small entrance incision formed in a patient's body using a trocar or obturator. For example, laparoscopic surgical procedures are performed within the abdominal cavity through small incisions formed in the abdominal wall. During a laparoscopic procedure, insufflating gases are introduced into the abdominal cavity to raise the abdominal wall or peritoneum away from the vital organs within the abdominal cavity, thereby providing an adequate region in which to operate.

During a laparoscopic procedure, it is necessary to maintain the atmospheric integrity of the abdominal cavity, and thus prohibit the egress of insufflation gases from the surgical site. It is common therefore, to provide a seal assembly within the cannula so that when instruments are present within the cannula and when instruments are withdrawn from the cannula, the tubular passageway extending therethrough is tightly sealed to prevent the egress of insufflating gases. For example, it is known to employ an elastomeric seal member with an aperture or slit that may be forced open when the instrument is passed therethrough. The seal member prevents the egress of insufflation gases when the instrument is present and absent from the cannula. There are known disadvantages to employing such seals. In particular, the opening or slit can tear when an instrument is forced therethrough, thus rendering the seal ineffective to prevent the egress of insufflating gases from the cannula sleeve.

Therefore as will be described hereinbelow, surgical instrument 900 has been equipped with the valve assembly of the present invention to prevent the egress of insufflating gases through the cannula in the absence of a surgical instrument. Surgical instrument 900 is intended for use as an access device, and more particularly, as a device to facilitate the introduction of a surgical instrument into a person's body during a minimally invasive surgical procedure. Surgical instruments introduced into a patient's body through the surgical instrument 900 of the subject invention can include, for example, clip appliers, graspers, dissectors, retractors, staplers, laser fibers, photographic devices, endoscopes, laparoscopes, tubes; and the like.

Surgical instrument or access device 900 includes a proximal valve housing 910 having an inlet port 912 for receiving surgical instruments. Valve housing 910 includes an upper body portion 920 and a lower body portion 930 which define, among other things, a generally hemispherical internal chamber 916 for accommodating a generally spherical valve member 950. Internal chamber 916 communicates with an outlet port 914 of the valve housing 910 which is axially aligned with the inlet port 912. Valve housing 910 is operatively associated with a lower cannula housing 980. Preferably, the valve housing 910 and cannula housing 980 are formed of a polycarbonate material.

An elongated cannula sleeve 982 extends distally from the cannula housing 980. Cannula sleeve 982 has an elongated passageway 984 extending therethrough, which defines a longitudinal axis defined by reference character "X". Passageway 984 is axially aligned with the inlet port 912 and outlet port 914 of valve housing 910. Cannula sleeve 982 may be formed of stainless steel or another suitable rigid material such as polycarbonate materials or the like. An inlet conduit 986 is incorporated into cannula housing 980 to permit the passage of insufflation gases through the cannula sleeve 982 and into the patient's body cavity. The inlet conduit 986 can include a stopcock valve, which is not shown.

Valve member 950, which is preferably formed from a polycarbonate material, is mounted for axial rotation within the interior chamber 916 about an axis extending perpendicular to the longitudinal axis of the cannula sleeve 982. Diametrically opposed pivot pins 958 (only one pin is shown in FIG. 16) extend radially outwardly from the surface of valve member 950 for accommodation within diametrically opposed recesses 932a, 932b to facilitate the axial rotation of valve member 950. An axial bore 952 extends through the valve member 950, and a convex sealing surface 954 is provided on valve member 950, spaced from axial bore 952.

Figure 17A:
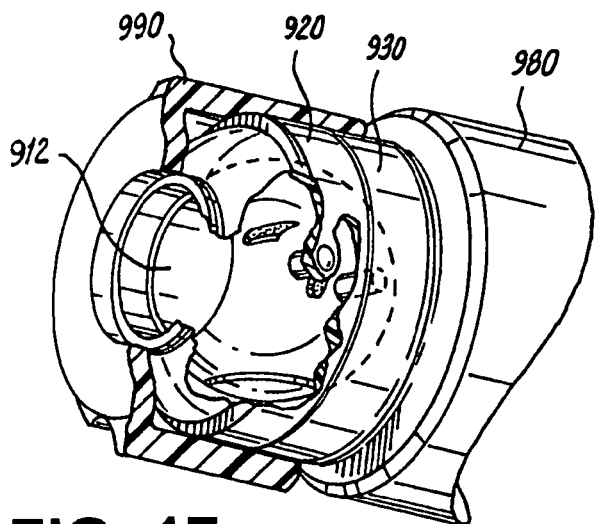
FIG. 17a is a perspective view in partial cross-section of the valve housing, which forms part of the surgical access device of FIG. 15, wherein the valve member is shown in an open position with the axial bore of the valve member aligned with the axially aligned inlet and outlet ports of the valve.

Valve member 950 is mounted for movement between an open position and a closed position. In the open position of valve member 950, which is shown in FIG. 17a. The axial bore 952 is axially aligned with the elongated passageway 984 of cannula sleeve 982 and the inlet and outlet ports 912, 914 of valve housing 910. In the closed position of valve member 950, which is shown in FIG. 17c, the axial bore 952 extends perpendicular to the elongated passageway 984 of cannula sleeve 982 and the sealing surface 954 is axially aligned with the inlet port 912 of valve housing 910.

Figure 17B:
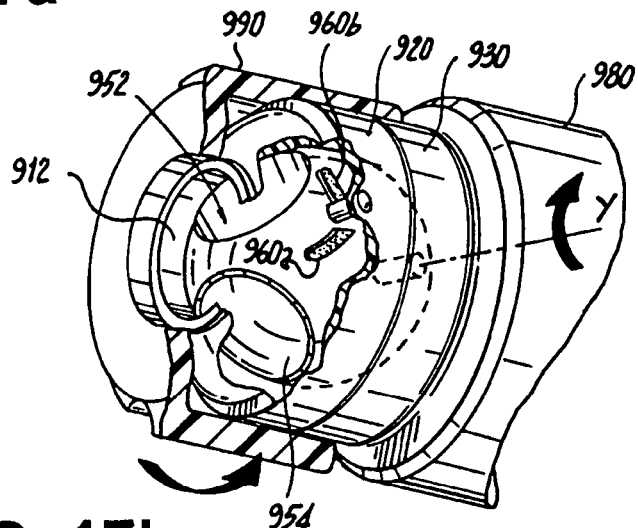
FIG. 17b is a perspective view in partial cross-section of the valve housing of the subject invention, wherein the valve member is in transition from the open position of FIG. 17a to the closed position of FIG. 17c.
Figure 17C:
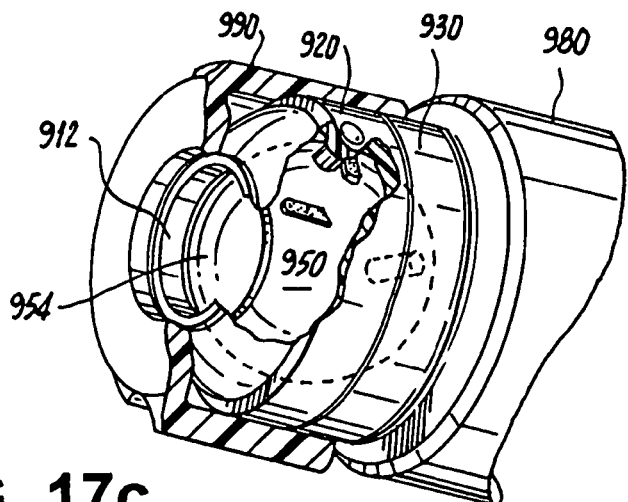
FIG. 17c is a perspective view in partial cross-section of the valve housing of the subject invention, wherein the valve member is disposed in a closed position so that the axial bore of the valve member is oriented perpendicular to the axially aligned inlet and outlet ports of the valve housing.

As described with respect to previous embodiments, a camming mechanism is operatively associated with the valve housing 910 and the valve member 950 for moving the valve member 950 between the open position of FIG. 17a and the closed position of FIG. 17c. The camming mechanism includes arcuate cam lobes 960a, 960b formed on the exterior surface of the valve member 950 and a cam pin 922 which extends radially inwardly from the interior surface of the upper housing portion/drive ring 920 to cooperate with the cam lobes. As before, a leading edge of the cam lobes 960a, 960b interacts with the cam pin 922. This interaction facilitates movement of the valve member 950 when the driving ring 920 is rotated about the longitudinal axis "X" of cannula sleeve 982. When the valve member 950 is moved between the open and closed positions, it is rotated about the pivot axis "Y" which extends through the pivot pin 958 of valve member 950, as illustrated in FIG. 17b.

Drive ring 920 is rotatably mounted on the proximal end of valve housing 910 and includes diametrically opposed radially inwardly extending guide ribs 924 which cooperate with an annular guide surface 938 formed on the exterior of the lower body portion 930 of the valve housing 910. Stop surfaces 940 limit the rotational motion of upper body portion/drive ring 920 relative to the longitudinal axis of the cannula sleeve 982.

A fluted manipulation knob 990 is cooperatively engaged with the drive ring 920. Manipulation knob 990 includes inlet port 992, which is aligned with the axial passageway 984 of cannula sleeve 982 and defines in part the inlet port 912 of valve housing 910. The engagement of drive ring 920 and manipulation knob 990 is accomplished through the coupling of a pair of diametrically opposed radially outwardly extending engagement tabs 926 on drive ring 920 (only one tab is shown in FIG. 16) with a pair of corresponding diametrically opposed interior recess 994a, 994b formed in the interior cavity of manipulation knob 990. Alternative structural means may be provided to enable ready manipulation of drive ring 920.

A flange 942 projects radially outwardly from the lower portion 930 of valve housing 910 to provide leverage to the surgeon when the manipulation knob 990 is rotated. Valve housing 910 further includes a membrane seal 996 located proximal to the interior chamber 916 and retained within an annular recess. Membrane seal 996 has a central slitted opening 998 that is axially aligned with the outlet port 912 of valve housing 910 and the passageway 984 of the cannula sleeve 982. Central opening 998 is dimensioned and configured to accommodate the passage of a surgical instrument therethrough. The membrane seal 996 will help to prevent the egress of insufflation gasses from the access device 900 when an instrument is present therein and the valve member 950 is in an open position.

Referring now to FIGS. 18 and 19, there is a perspective view of another embodiment of the surgical access device of the subject invention, which is designated by reference numeral 1000 and includes a detachable valve housing 1010. More particularly, as best seen in FIG. 19, the valve housing 1010 is detachably connected to the cannula housing 1080. This will enable a surgeon to utilize the cannula housing 1080 during the performance of procedures in which the valve housing is not required. It will also enable the surgeon to readily remove specimens from the surgical site. As illustrated, the detachable relationship of valve housing 1010 and cannula housing 1080 is facilitated by a threaded connection therebetween. Alternative coupling arrangements are envisioned and well within the scope of the subject disclosure.

Although the valve assembly of the subject invention and surgical access device incorporating the same have been described with respect to preferred embodiments, those skilled in the art will readily appreciate that changes and modifications may be made thereto without departing from the spirit and scope of the subject invention as defined by the appended claims.

Additionally, the valve assembly of the subject invention can be used in alternative applications not described hereinabove. For example, the valve can be installed in a sink drain to eliminate the need for a plug. Additionally, the valve can replace bungs or plugs used to seal penetrations in the hull of boats. Still further, the valve can replace caps on hand creams, toothpaste, etc.

The following descriptions were previously incorporated by reference to New Zealand Provisional Patent Application Serial No. 526158, filed May 29, 2003, entitled "Rotating Sealing Mechanism."

The device is a new form of valve or sealing mechanism. The device will seal or unseal to allow matter to pass through the device.

The device cart be attached to or form part of, a container of any size or shape or a tube, pipe, conduit or other space designed to contain or enable the passage or flow of matter.

The device can form the middle or joining or end or finishing point between two or more spaces, containers, tubes, pipes or conduits either by being attached to or forming part of one or more of the spaces, containers, tubes, pipes or conduits.

When the device is open it enables matter within the space, container, tube, pipe or conduit to pass through the device in either direction. When the device is closed it prevents the movement of matter from one side of the device to the other.

The device enables the sealing and unseating or closing and opening of the space container, tube, pipe or conduit:
  without needing to separate or remove a top, lid, cap, coyer or separate form of closure from the space, container, tubs, pipe or conduit;
  using one or more turning, twisting, pulling, pushing or rotating movements of the device;
  from fully open to completely sealed with one at more movements using one or more points of pressure.

The device enables the matter within the space, container, tube, pipe or conduit to move directly from the space, container, tube, pipe or conduit without passing through any retarding or flow inhibiting elements.

The device has many potential applications. For example, it could be used to seal or unseat or open or close a bottle, pipe, tube, petrol opening on vehicles, medical openings, sinks.

The device is composed of at least two elements:
The Core
The Top Housing
The Lower Housing
The Core The Core may be constructed, made or formed of arty rigid, semi-rigid, hard or semi-hard material such as plastic, rubber or metal. The Core pivots or rotates around an axis. The Core integrates one or more pivoting points fixed at the axis which enable the rotation. The Core seals or unseals depending on which face is presented to the hole, opening or aperture of the Housing. The Core integrates the rack element of device. The Core integrates an internal hole, opening or aperture which passes from one face of the core to the other. The Core may be spherical, semi-spherical, or any other curved or semi-rounded surface or similar shape.

The Top Housing

The Top Housing integrates a hole, opening or aperture. The Top Housing integrates a pinion. The Top Housing integrates elements that attach the Top Housing either permanently or non-permanently to the lower Housing. The Top Housing slides, rotates or moves against the Lower Housing. The Top Housing integrates elements that restrict the degree of slide, rotation or movement of the Top Housing against the Lower Housing. The Top Housing may be constructed, made or formed of arty rigid, semi-rigid, hard or semi-hard material such as plastic, rubber or metal.

The Lower Housing

The Lower Housing may be attached to or may form part of a container of any size or shape or a tube, pipe, conduit or other space designed to contain or enable the passage or flow of matter. The Lower Housing integrates gaps, bracket or space against which the pivot points rotate or turn. The Lower Housing integrates a hole, opening or aperture. The Lower Housing slides, rotates or moves against the Lower Housing. The Lower Housing integrates elements that restrict the degree of slide, rotation or movement of the Lower Housing against the Top Housing. The Lower Housing may be constructed, made or formed of any rigid, semi-rigid, hard or semi-hard material such as plastic, rubber or metal.

Operation

The device utilizes a spherical, semi-spherical, or any other curved or semi-rounded surface or similar shape to seal a hole, opening or aperture. This Core (see above) slides, turns, moves or rotates on a rack and pinion type mechanism to go from closed to open, and in reverse, from open to closed, by twisting, turning, rotating or moving against the Top Housing and or the Lower Housing.

The device is operated by applying a turning, twisting, pushing, pulling or rotating motion to either the top or lower housing, which applies force to the Core which then rotates or moves to seal or unseal the opening, aperture or hole by presenting either the Core's internal hole to unseal or any other face of the Core to seal.

What is claimed is:

1. A valve assembly suitable for use in controlling a fluid flow, said valve assembly comprising:
   a) a valve housing including
      i) an upper body portion and a lower body portion, the upper and lower body portions defining
      ii) an internal chamber suitable for accommodating a valve member configured in a pivoting relationship with the valve housing, and the valve housing defining an inlet port and an outlet port, the inlet port and the outlet port being axially aligned and being formed in the upper and lower body portions, respectively;
   b) a generally spherical valve member seatable within the internal chamber of the valve housing and including
      i) an axial bore extending therethrough,
      ii) the valve member mounted for movement between an open position wherein the axial bore of the valve member is axially aligned with the inlet port and outlet port of the valve housing to allow the flow of said fluid therethrough, and
      a closed position wherein the axial bore of the valve member is out of alignment with the inlet port and the outlet port of the valve housing;
   c) a camming mechanism for moving the valve member between the open position and the closed position when the upper body portion of the housing is rotated about a central axis with respect to the lower body portion; and the camming mechanism including cam surfaces formed on an exterior surface of the valve member and a cam pin formed on an interior surface of the upper body portion of the housing, wherein the cam surfaces formed on the exterior surface of the valve member are defined by a recess having a pair of reaction surfaces, the reaction surfaces being at an angle to one another.

2. The valve assembly as recited in claim 1, wherein the valve member is mounted for axial rotation within the interior chamber about an axis extending perpendicular to the central axis defined by the upper and lower body portion of the valve housing.

3. The valve assembly as recited in claim 1, wherein the housing includes means associated with the inlet port for engaging the valve with a receptacle or tubing.

4. The valve assembly as recited in claim 1, wherein the housing includes means associated with the outlet port for engaging the valve with a receptacle or tubing.

5. The valve assembly as recited in claim 1, wherein the sealing surface of the valve member includes an annular recess having an O-ring disposed therein.

6. The valve assembly as recited in claim 1, wherein the valve member has an outer radius which is larger than an inner radius of the valve seat so as to create an interference fit therewith when the valve assembly is in the closed position.

7. The valve assembly as recited in claim 1, further comprising a frangible ring engaged with an exterior of the valve housing to provide a visual indication of whether the valve has been opened.

8. The valve assembly as recited in claim 1, further comprising a frangible sealing disc inserted into the interior chamber of the valve to provide a visual indication of whether the valve has been opened and wherein the valve member includes means for puncturing the disc when the valve is opened.

9. The valve assembly as recited in claim 1, wherein the axial bore of the valve member is adapted and configured for receiving and storing an article of manufacture when the valve is in the closed position.

10. The valve assembly as recited in claim 1, further comprising means associated with the valve housing for facilitating the axial rotation of the lower body portion of the housing relative to the upper body portion.

11. The valve assembly as recited in claim 1, wherein a plurality of flow passages are formed in the valve member extending therethrough along an axis which is perpendicular to the axial bore such that when the valve is in the closed position, fluid or air traverses the valve through the plurality of flow passages.

12. The valve assembly as recited in claim 1, wherein the valve member moves between the open position and the closed position when the upper body portion of the housing is rotated about the central axis between about 57 degrees and about 77 degrees with respect to the lower body portion.

13. The valve assembly as recited in claim 1, further comprising a telescoping nozzle or sleeve disposed within the aperture of the valve member.

14. A surgical access device comprising:
   a) a valve housing defining a valve seat for accommodating a valve member, and having an inlet port and an outlet port, the inlet port and the outlet port being axially aligned;

b) an elongated cannula sleeve operatively associated with the valve housing and including a passageway extending therethrough which defines a longitudinal axis aligned with the inlet port and the outlet port of the valve housing;

c) a generally spherical valve member seatable within the valve housing and having an axial bore extending therethrough, the valve member being mounted for movement between an open position wherein the axial bore of the valve member is axially aligned with the passageway of the cannula sleeve and the inlet port and outlet port of the valve housing, and a closed position wherein the axial bore of the valve member extends perpendicular to the passageway of the cannula sleeve and the inlet port and outlet port of the valve housing; and d) a camming mechanism including cam surfaces formed on an exterior surface of the valve member and a cam pin mounted for movement relative to the cam surfaces of the valve member, wherein the cam pin extends radially inwardly from a drive ring supported on the valve housing and mounted for rotation about the longitudinal axis of the cannula sleeve, and wherein rotation of the drive ring causes corresponding rotation of the valve member within the valve seat of the valve housing, and wherein the cam surfaces formed on the exterior surface of the valve member are defined by a recess having a pair of reaction surfaces, the reaction surfaces being at an angle to one another.

15. The surgical access device as recited in claim 14, wherein the valve member is mounted for axial rotation within the valve seat about an axis extending perpendicular to the axially aligned inlet and outlet ports of the valve housing.

16. The surgical access device as recited in claim 14, wherein the access device further includes a membrane seal located proximal to the valve seat, the membrane seal having an opening axially aligned with the elongated passageway of the cannula sleeve dimensioned to accommodate the passage of a surgical instrument therethrough.

17. The surgical access device as recited in claim 14, wherein the cannula sleeve depends from a cannula housing associated with the valve housing.

18. The surgical access device as recited in claim 17, wherein the cannula housing is detachably connected to the valve housing.

19. The surgical access device as recited in claim 14, wherein the valve member includes a convex sealing surface, which is aligned with the inlet port of the valve housing when the valve member is in the closed position.

20. The surgical access device as recited in claim 14, wherein the valve member includes a sealing surface adapted for sealing engagement with the valve seat formed in the housing when the valve is in the closed position.

21. The surgical access device as recited in claim 20, wherein the sealing surface of the valve member includes an annular recess having an O-ring disposed therein.

22. A valve assembly comprising:

a) a valve housing defining a valve seat for accommodating a valve member, and including an inlet port and an outlet port, the inlet port and the outlet port being axially aligned;

b) a generally spherical valve member seated within the valve housing and having an axial bore extending therethrough, the valve member mounted for movement between an open position wherein the axial bore of the valve member is axially aligned with the inlet port and outlet port of the valve housing, and a closed position wherein the axial bore of the valve member is out of alignment with the inlet and outlet ports of the valve housing to restrict flow therethrough; and c) camming means operatively associated with the valve housing and the valve member for moving the valve member between the open position and the closed position;

the camming mechanism including cam surfaces formed on an exterior surface of the valve member and a cam pin mounted for movement relative to the cam surfaces of the valve member, wherein the cam surfaces formed on the exterior surface of the valve member are defined by a recess having a pair of reaction surfaces, the reaction surfaces being at an angle to one another.

23. The valve assembly as recited in claim 22, wherein the valve member is mounted for rotation within the valve seat about an axis extending perpendicular to the inlet port and outlet port of the valve housing.

24. The valve assembly as recited in claim 22, wherein the means operatively associated with the valve housing and the valve member for moving the valve member between the open position and the closed position includes a camming mechanism.

25. The valve assembly as recited in claim 22, wherein the housing includes means associated with the inlet port for engaging the valve with a receptacle or tubing.

26. The valve assembly as recited in claim 22, wherein the housing includes means associated with the outlet port for engaging the valve with a receptacle or tubing.

27. The valve assembly as recited in claim 22, further comprising a frangible ring engaged with an exterior of the valve housing to provide a visual indication of whether the valve has been opened.

28. The valve assembly as recited in claim 22, further comprising a frangible sealing disc inserted into the interior chamber of the valve to provide a visual indication of whether the valve has been opened and wherein the valve member includes means for puncturing the disc when the valve is opened.

29. The valve assembly as recited in claim 22, wherein the axial bore of the valve member is adapted and configured for receiving and storing an article of manufacture when the valve is in the closed position.

30. The valve assembly as recited in claim 22, further comprising means associated with the valve housing for facilitating the axial rotation of the lower body portion of the housing relative to the upper body portion.

31. The valve assembly as recited in claim 22, wherein a plurality of flow passages are formed in the valve member extending therethrough along an axis which is perpendicular to the axial bore such that when the valve is in the closed position, fluid or air traverses the valve through the plurality of flow passages.

32. The valve assembly as recited in claim 22, wherein the valve member moves between the open position and the closed position when an upper body portion of the housing is rotated about the central axis between about 57 degrees and about 77 degrees with respect to a lower body portion of the housing.

33. The valve assembly as recited in claim 22, wherein the valve member has an outer radius which is larger than an inner radius of the valve seat so as to create an interference fit therewith when the valve assembly is in the closed position.

34. The valve assembly as recited in claim 22, further comprising a telescoping nozzle or sleeve disposed within the axial bore of the valve member.

* * * * *